United States Patent
Xu et al.

(10) Patent No.: US 9,360,585 B2
(45) Date of Patent: Jun. 7, 2016

(54) BOREHOLE INDEPENDENT NEUTRON POROSITY MEASUREMENT

(75) Inventors: Libai Xu, Katy, TX (US); Cornelis Huiszoon, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1192 days.

(21) Appl. No.: 13/113,696

(22) Filed: May 23, 2011

(65) Prior Publication Data

US 2012/0303280 A1    Nov. 29, 2012

(51) Int. Cl.
*G01V 5/10* (2006.01)
*G01N 15/08* (2006.01)
*E21B 47/10* (2012.01)

(52) U.S. Cl.
CPC *G01V 5/10* (2013.01); *G01N 15/08* (2013.01); *G01V 5/107* (2013.01); *E21B 47/1015* (2013.01)

(58) Field of Classification Search
CPC .......... G01V 5/10; G01V 5/107; G01N 15/08
USPC ...................................... 250/269.4
See application file for complete search history.

(56) References Cited

U.S. PATENT DOCUMENTS

| | | | |
|---|---|---|---|
| 3,483,376 A | 12/1969 | Locke | |
| 4,423,323 A | 12/1983 | Ellis | |
| 4,570,067 A | 2/1986 | Gadeken | |
| 4,638,158 A | 1/1987 | Sonne | |
| 5,019,708 A * | 5/1991 | Flaum | 250/264 |
| 5,473,158 A | 12/1995 | Holenka et al. | |
| 5,486,695 A | 1/1996 | Schultz et al. | |
| 5,767,510 A | 6/1998 | Evans | |
| 5,825,024 A | 10/1998 | Badruzzaman | |
| 5,900,627 A | 5/1999 | Odom | |
| 6,297,507 B1 | 10/2001 | Chen | |
| 6,781,115 B2 | 8/2004 | Stoller | |
| 6,894,274 B2 | 5/2005 | Valant-Spaight | |
| 7,294,829 B2 | 11/2007 | Gilchrist | |
| 7,365,307 B2 | 4/2008 | Stoller | |
| 2002/0190198 A1 | 12/2002 | Mickael | |
| 2007/0057171 A1 * | 3/2007 | Stoller | G01V 5/107 250/253 |
| 2010/0145621 A1 * | 6/2010 | Moake | 702/8 |
| 2010/0282976 A1 | 11/2010 | Le Tourneur | |

FOREIGN PATENT DOCUMENTS

EP    1686396 B1    6/2009
RU    2396579 C2    8/2010

OTHER PUBLICATIONS

International Search Report and Written Opinion issued in PCT/US2012/039221 on Aug. 30, 2012, 6 pages.

(Continued)

*Primary Examiner* — David Porta
*Assistant Examiner* — Mindy Vu
(74) *Attorney, Agent, or Firm* — Kimberly Ballew

(57) ABSTRACT

A method for estimating a borehole independent porosity of a subterranean formation includes processing a neutron logging data point, preferably including average near and far detector neutron count rates with suitable input data to obtain the porosity estimate. The borehole independent formation porosity may be obtained without any compensation and without any reliance on the measurement or estimation of sensor standoff and/or borehole caliper.

8 Claims, 12 Drawing Sheets

(56) References Cited

OTHER PUBLICATIONS

GE Energy; "Reuter stokes helium-3 filled position sensitive proportional counter—RS-P4-0424-201" 2005 General Electric Company.

Gilchrist, W.A., Jr.; "Compensated neutron log response issues—A tutorial" SPWLA 49th Annual Logging Symposium, Edinburgh, Scotland, May 25-28, 2008.

Ellis, Darwin V., et al; "Porosity from neutron logs I: Measurement" Petrophysics, vol. 44, No. 6, Nov.-Dec. 2003; p. 383-395.

Ellis, Darwin V., et al; "Porosity from neutron logs II: Interpretation" Petrophysics, vol. 45, No. 1, Jan.-Feb. 2004; p. 73-86.

Athanasiades, Athanasios, et al.; "Straw detector for high rate, high resolution neutron imaging" 2005 IEEE Nuclear Science Symposium Conference Record, pp. 623-627.

Thermo Scientific; "Thermo scientific API120; A compact, portable neutron generator for associated particle imaging" 2008, www.thermo.com/neutron.

Jacobson, Larry, et al.; "An improved formation density measurement using PNC Tools" SPE Annual Technical Conference and Exhibition, Houston, TX Sep. 26-29, 2004, SPE 90708.

Neuman, C.H., et al.; "An investigation of density derived from pulsed neutron capture measurements" SPE Annual Technical Conference and Exhibition, Houston, TX Oct. 3-6, 1999, SPE 56647.

Odom, Richard, et al.; "Improvements in a through-casing pulsed-neutron density log" SPE Annual Technical Conference and Exhibition, New Orleans, LA Sep. 30-Oct. 3, 2001 SPE71742.

Weller, Geoff, et al.; "A new integrated LWD platform brings next-generation formation evaluation services" Socited of Petrophysicists and Well Log Analysis (SPWLA) 46th Annual Logging Symposium, New Orleans, LA Jun. 26-29, 2005.

* cited by examiner

BOREHOLE INDEPENDENT NEUTRON POROSITY MEASUREMENT

RELATED APPLICATIONS

None.

FIELD OF THE INVENTION

The present invention relates generally to neutron logging of a subterranean borehole. In particular, this invention relates to a method for making neutron porosity logging measurements of a subterranean formation independent of sensor standoff and borehole caliper.

BACKGROUND OF THE INVENTION

During hydrocarbon exploration and production, the pore space or "porosity" of a formation is an important property for evaluating the hydrocarbon bearing potential of the formation. Neutron logging measurements are commonly made to obtain a formation porosity estimate. In conventional neutron logging operations, a neutron source emits high energy ("fast") neutrons into the formation. These fast neutrons are slowed by the surrounding formation (particularly via collisions with hydrogen nuclei present in the formation and the borehole) and eventually captured. The capture of a neutron may result in the emission of one or more prompt capture gamma rays. While, neutron logging tools can be configured to detect the capture gamma rays, epithermal and/or thermal (slowed) neutrons are most commonly detected using neutron detectors deployed on the logging tool.

U.S. Pat. No. 3,483,376 to Locke discloses a system for making neutron porosity measurements. The system includes a neutron source deployed in a tool body in close proximity to and longitudinally spaced from first and second longitudinally spaced neutron detectors (commonly referred to in the art as near and far detectors). The ratio of the neutron count rates measured at the corresponding near and far detectors (the near to far ratio) was found to be more sensitive to formation porosity than to other borehole parameters (e.g., to borehole diameter, borehole shape, or sensor standoff). This ratio has therefore become a common measurement parameter used to compute formation porosity. To this day neutron logging tools commonly make use of axially spaced near and far detectors and the aforementioned near to far ratio to compute neutron porosity.

In general the near to far ratio tends to increase monotonically with increasing porosity. This relationship is commonly (and generally) understood in the industry as follows. Formations having high porosity generally slow down fast neutrons more efficiently than low porosity formations due to the higher concentration of hydrogen in the formation (in the form of water or hydrocarbon in the pore space). In a highly porous formation, the neutrons therefore tend to be captured nearer to the source which typically results in a relatively small number of neutrons being detected at the far detector and therefore a correspondingly high near to far ratio. In less porous formations the emitted neutrons tend to travel farther into the formation resulting in a comparatively higher count rate at both detectors and a correspondingly lower near to far ratio.

While the use of dual (near and far) detectors was intended to minimize the effects of the borehole upon the measured formation porosity, it is well known that neutron porosity measurements continue to be adversely affected by changes in the measurement conditions. For example, borehole size and shape, sensor standoff, drilling fluid weight and salinity, and borehole temperature and pressure are all known to impact the near to far ratio and therefore the neutron porosity measurement. Commercial neutron porosity tools are commonly calibrated for well defined, standard borehole conditions. Variations from these standard conditions can adversely affect the quality of the obtained porosity measurements. Corrections for borehole size and sensor standoff are routinely made to neutron porosity measurements using direct standoff and caliper measurements or standoff and caliper estimates made using various other measurements.

The prior art includes several attempts to improve neutron porosity compensation (or correction) using corresponding ultrasonic standoff and/or caliper measurements. For example, U.S. Pat. No. 4,423,323 to Ellis et al discloses a methodology in which a borehole correction is applied to wireline neutron data. The borehole correction is applied to the neutron data prior to computing neutron porosity and requires a corresponding borehole caliper measurement. U.S. Pat. No. 5,486,695 to Schultz et al discloses a methodology by which LWD sensor data is compensated by applying a standoff weighting factor based on corresponding standoff measurements.

U.S. Pat. No. 5,767,510 to Evans claims to disclose a method for obtaining a neutron porosity measurement that requires no independent measure of borehole geometry. Such "borehole invariance" (as it is termed) is obtained by compensating the far detector so that its borehole sensitivity (referred to as radial sensitivity) matches the borehole sensitivity of the near detector. One drawback with the disclosed method is that such compensation also tends to reduce the sensitivity of the far detector (and therefore the far to near count ratio) to formation porosity. Reduced sensitivity can in turn lead to an unreliable (or noisy) porosity measurement (due to poor statistics). Furthermore, the borehole invariance method requires a knowledge of drilling fluid weight and salinity in order to modify the far detector count rate. As is well known to those of ordinary skill in the art, these drilling fluid parameters are often not well known in-situ.

U.S. Pat. No. 6,894,274 to Valant-Spaight discloses a method in which neutron count rates obtained in water are subtracted from the count rates obtained in the borehole. While this "water compensation" methodology tends to provide improved compensation in low porosity formations, the errors obtained in high porosity formations can be unacceptably large.

Despite the fact that neutron logging techniques have been in commercial use for over 50 years, the interpretation of neutron logs remains challenging and problematic. There is clearly a need in the art for improved methods for making and interpreting neutron logging measurements. In particular there is a need for a method that provides compensation for changes in borehole geometry without requiring measurements thereof (e.g., without requiring corresponding standoff and/or caliper measurements).

SUMMARY OF THE INVENTION

Exemplary aspects of the present invention are intended to address the above described need for improved neutron logging tools and methods. Aspects of the invention may be utilized to estimate a borehole independent porosity of a subterranean formation. A single neutron logging data point, preferably including average near and far detector neutron count rates, may be processed in combination with suitable input data to obtain the borehole independent formation porosity. The borehole independent formation porosity may be obtained without any compensation and is advantageously substantially independent of borehole diameter, borehole shape, and sensor standoff.

Exemplary embodiments of the present invention advantageously enable accurate and robust neutron porosity measurements to be made without any compensation and without reliance on the measurement or estimation of sensor standoff and/or borehole caliper. The present invention also enables a more precise formation porosity measurement to be made since all data (e.g., collected while the tool is rotating in the borehole) may be utilized. Those of ordinary skill in the art will readily appreciate that utilizing all collected data advantageously tends to minimizes statistical error. Moreover, neutron porosity measurements made in accordance with the present invention tend to be less affected by borehole rugosity and irregular boreholes where acoustic-based standoff measurements can be problematic.

In one aspect the present invention includes a method for estimating formation porosity from a neutron logging measurement. A neutron logging data point including a near count rate and a far count rate is acquired. Input data is also acquired. The input data relates near count rate, far count rate, and formation porosity in a region of interest, the region of interest including a predetermined range of borehole diameter and a predetermined range of sensor standoff. The data point and the input data are then processed to obtain a borehole independent formation porosity.

In another aspect the present invention includes a method for estimating formation porosity from a neutron logging measurement. A neutron logging data point including first near and far count rates is acquired. A porosity intercept point including second near and far count rates is also acquired. A slope is computed from the acquired data point and the porosity intercept point. A borehole independent formation porosity is then obtained from the computed slope.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
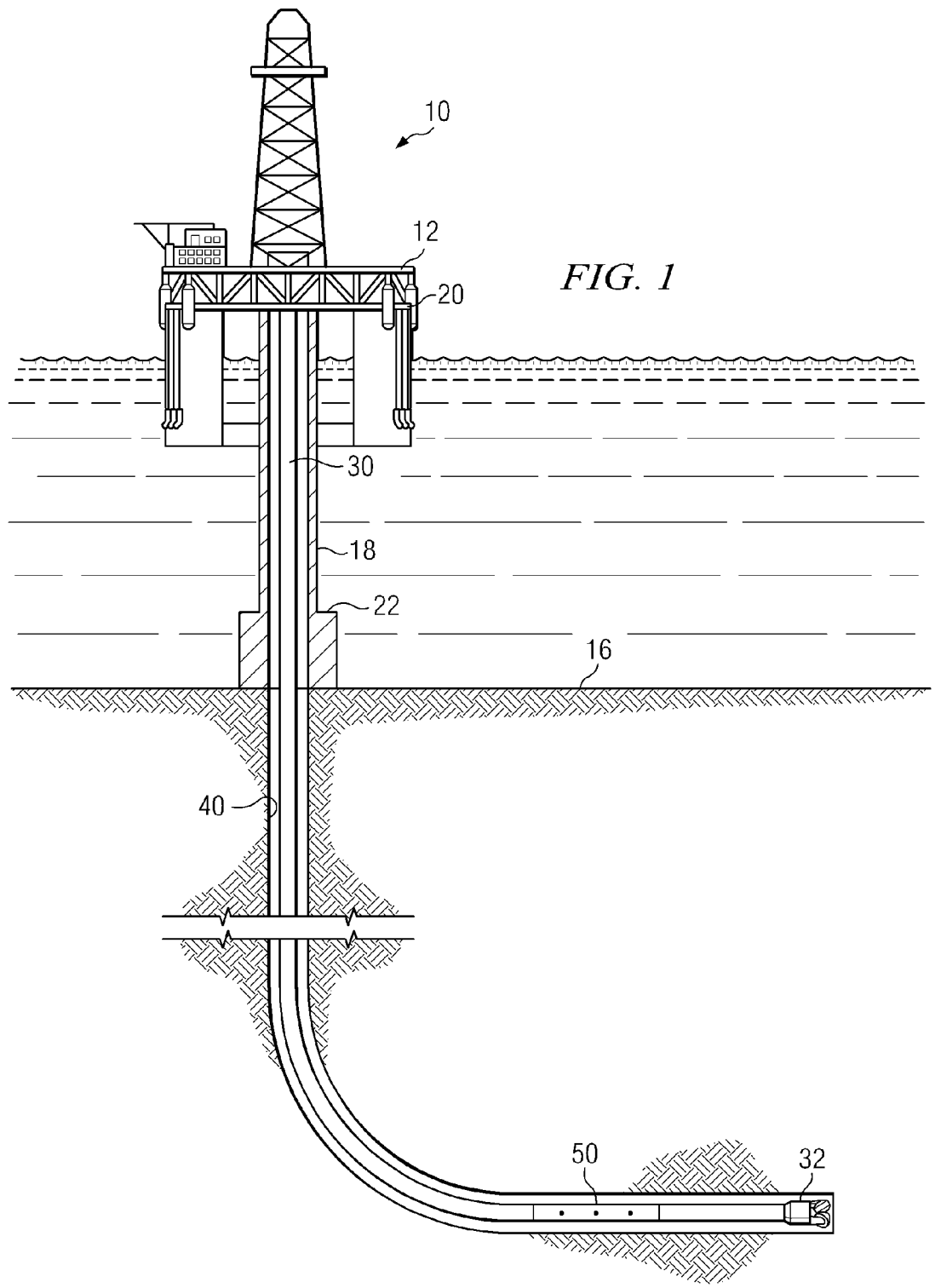
FIG. 1 depicts a conventional drilling rig on which exemplary embodiments of the present invention may be utilized.

FIG. 1 depicts one exemplary embodiment of a neutron logging tool 50 in use in an offshore oil or gas drilling assembly, generally denoted 10. In FIG. 2, a semisubmersible drilling platform 12 is positioned over an oil or gas formation disposed below the sea floor 16. A subsea conduit 18 extends from deck 20 of platform 12 to a wellhead installation 22. The platform may include a derrick and a hoisting apparatus for raising and lowering the drill string 30, which, as shown, extends into borehole 40 and includes a drill bit 32 and neutron logging tool 50. Embodiments of neutron logging tool 50 typically include at least one neutron source and first and second axially spaced neutron detectors. Drill string 30 may further include, for example, a downhole drill motor, a mud pulse telemetry system, a steering tool, and/or one or more of numerous other MWD and LWD sensors for sensing downhole characteristics of the borehole and the surrounding formation. The invention is not limited in these regards.

It will be understood by those of ordinary skill in the art that the deployment depicted on FIG. 1 is merely exemplary for purposes of describing the invention set forth herein. It will be further understood that methods in accordance with the present invention are not limited to use in offshore drilling operations. The inventive methods are equally well suited for use with any kind of subterranean drilling operation, either offshore or onshore. Moreover, while neutron logging tool 50 is shown coupled with drill string 30 on FIG. 1, it will be understood that the invention is not limited to logging while drilling embodiments. Methods in accordance with the present invention may also be utilized, for example, in neutron logging operations in which the logging tool is conveyed into the borehole using substantially any means of conveyance, for example, including wireline, slick line, coiled tubing, and the like.

As described above in the Background section, neutron logging measurements are commonly made using a logging tool having a neutron source (e.g., a sealed chemical source or an electrical source) deployed in a tool body in close proximity to (e.g., within a few feet) and longitudinally spaced from first and second longitudinally spaced neutron detectors. As also described above, the ratio of the count rate at the near detector to the count rate at the far detector is a common measurement parameter used to estimate formation porosity.

Figure 2A:
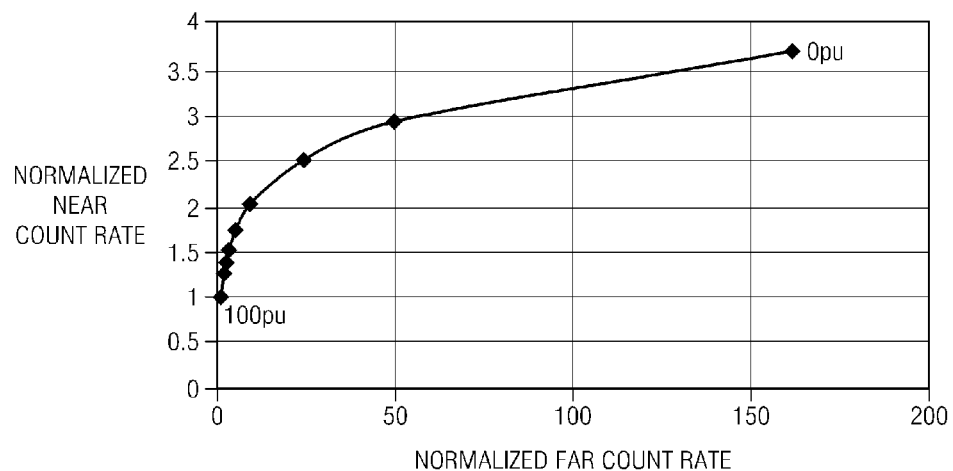
FIG. 2A depicts simulated data in a plot of average near count rate versus average far count rate for freshwater filled limestone in a standard borehole.

FIG. 2A depicts a plot of average near counts (on the y-axis) versus average far counts (on the x-axis) obtained using Monte Carlo simulations for freshwater filled limestone having porosities ranging from 0 to 100 percent (porosity units—pu). The simulations correspond to a PathFinder Energy Services SDNSC® neutron logging tool deployed in a standard condition borehole. The standard conditions refer to a six inch diameter borehole and a sensor standoff of zero inches. Other neutron logging tool embodiments and borehole conditions could be equivalently modeled (as the invention is of course not limited to any particular logging tool geometry). Average neutron counts were obtained by modeling rotation of the tool geometry through a full revolution at 22.5 degree increments. Both the near and far counts are normalized to unity for a water measurement. The plot depicted on FIG. 2A shows the relationship between the ration of the near count rate to the far count rate and formation porosity (i.e., the ratio generally increases with increasing porosity). It will be understood that the ratio of the near count rate to the far count rate is also referred to herein as the near to far ratio.

Figure 2B:
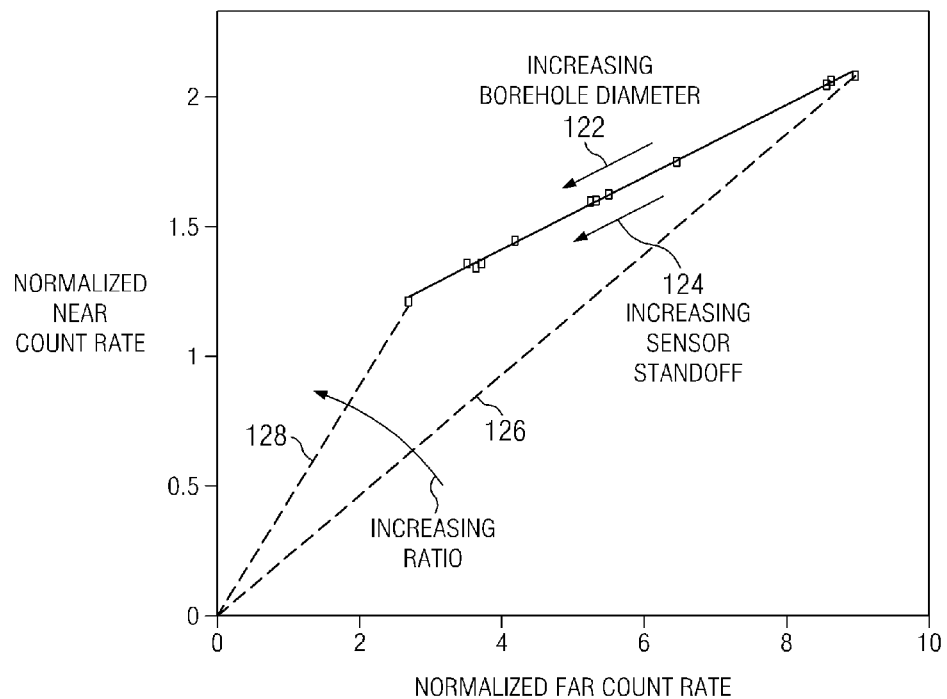
FIG. 2B depicts simulated data in a plot of average near count rate versus average far count rate for a 20 pu limestone formation at nonstandard borehole conditions.

FIG. 2B depicts a simulated plot of average near count rate versus average far count rate for a 20 pu limestone formation at nonstandard borehole conditions. In particular, the borehole diameter is in the range from 6 to 9 inches and the sensor standoff is in the range from 0 to 1.5 inches. Each of the near and far count rates were observed to decrease with increasing borehole diameter and increasing sensor standoff as indicated at 122 and 124. Moreover, as is known to those of ordinary skill in the art, the near to far ratio was also observed to increase as indicated at 126 and 128 with increasing borehole diameter and increasing sensor standoff (increasing slope of lines 126 and 128 indicates an increasing ratio). Absent suitable compensation, the increased near to far ratio may be falsely indicative of increased formation porosity (e.g. as indicated on FIG. 2A).

Figure 3A:
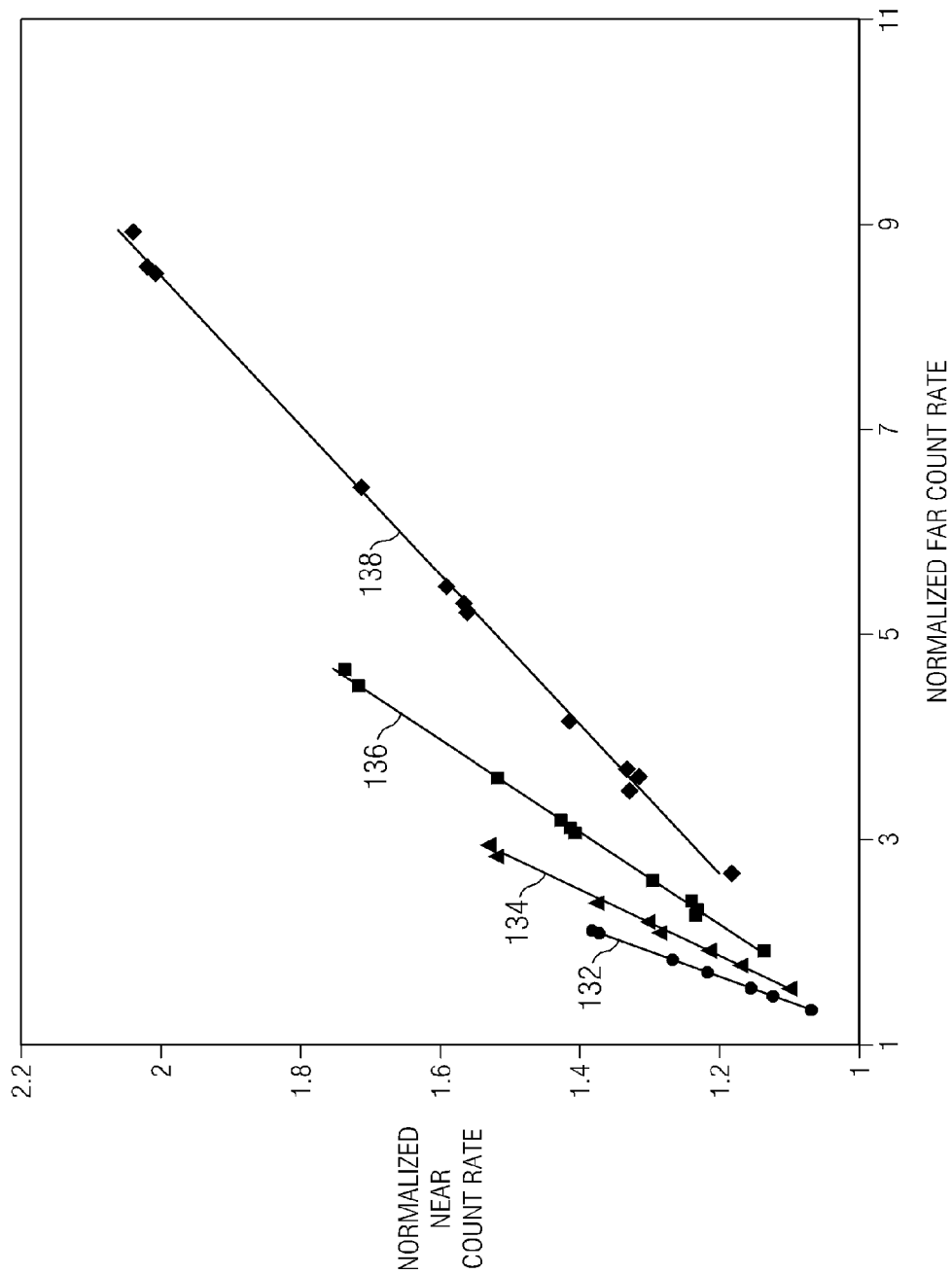
FIGS. 3A and 3B (collectively FIG. 3) depict simulated data in plots of average near count rate versus average far count rate for a number of formation porosities at nonstandard borehole conditions. Formation porosities of 50, 40, 30, and 20 pu are depicted on FIG. 3A while formation porosities of 20, 10, and 0 pu are depicted on FIG. 3B.
Figure 3B:
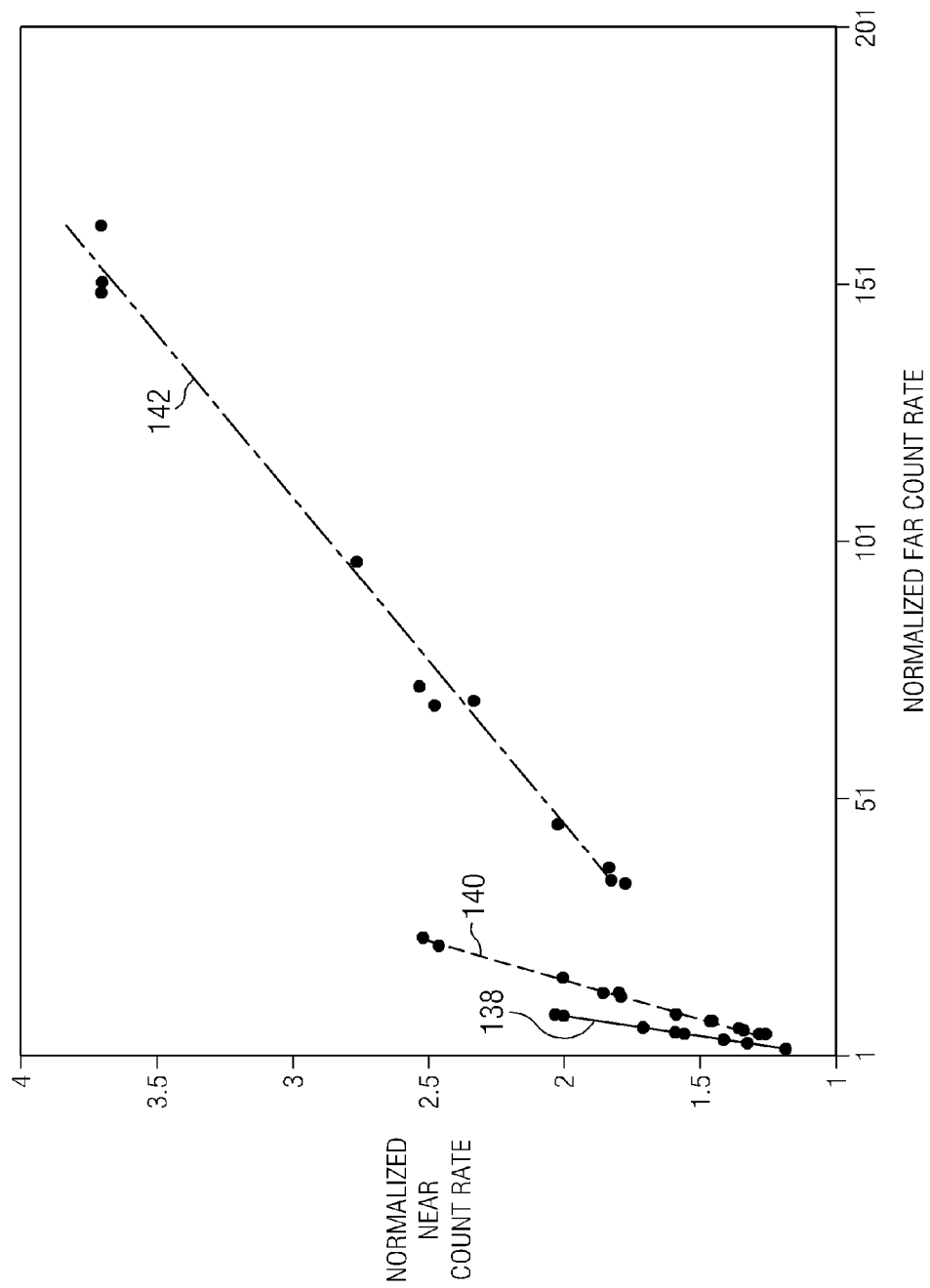

FIGS. 3A and 3B depict simulated average near count rate versus average far count rate for a number of formation porosities in the same borehole diameter and sensor standoff ranges described above. Formation porosities of 50, 40, 30, and 20 pu are depicted at 132, 134, 136, and 138 on FIG. 3A while formation porosities of 20, 10, and 0 pu are depicted at 138, 140, and 142 on FIG. 3B. One aspect of the present invention is the realization that varying the borehole diameter and sensor standoff (as described above) results in a unique curve for each formation porosity (in a near count rate versus far count rate plot). It was further realized that these unique curves are substantially linear and do not intersect one another within a selected range of borehole diameter and sensor standoff values (referred to herein as a region of interest). Since the curves do not intersect in the region of interest, each acquired data point (e.g., including an average near count rate and an average far count rate) corresponds to a unique formation porosity that is independent of the borehole conditions (referred to herein as a borehole independent formation porosity). The data point also corresponds to a unique borehole geometry parameter (which is a function of the borehole diameter and sensor standoff).

Figure 4:
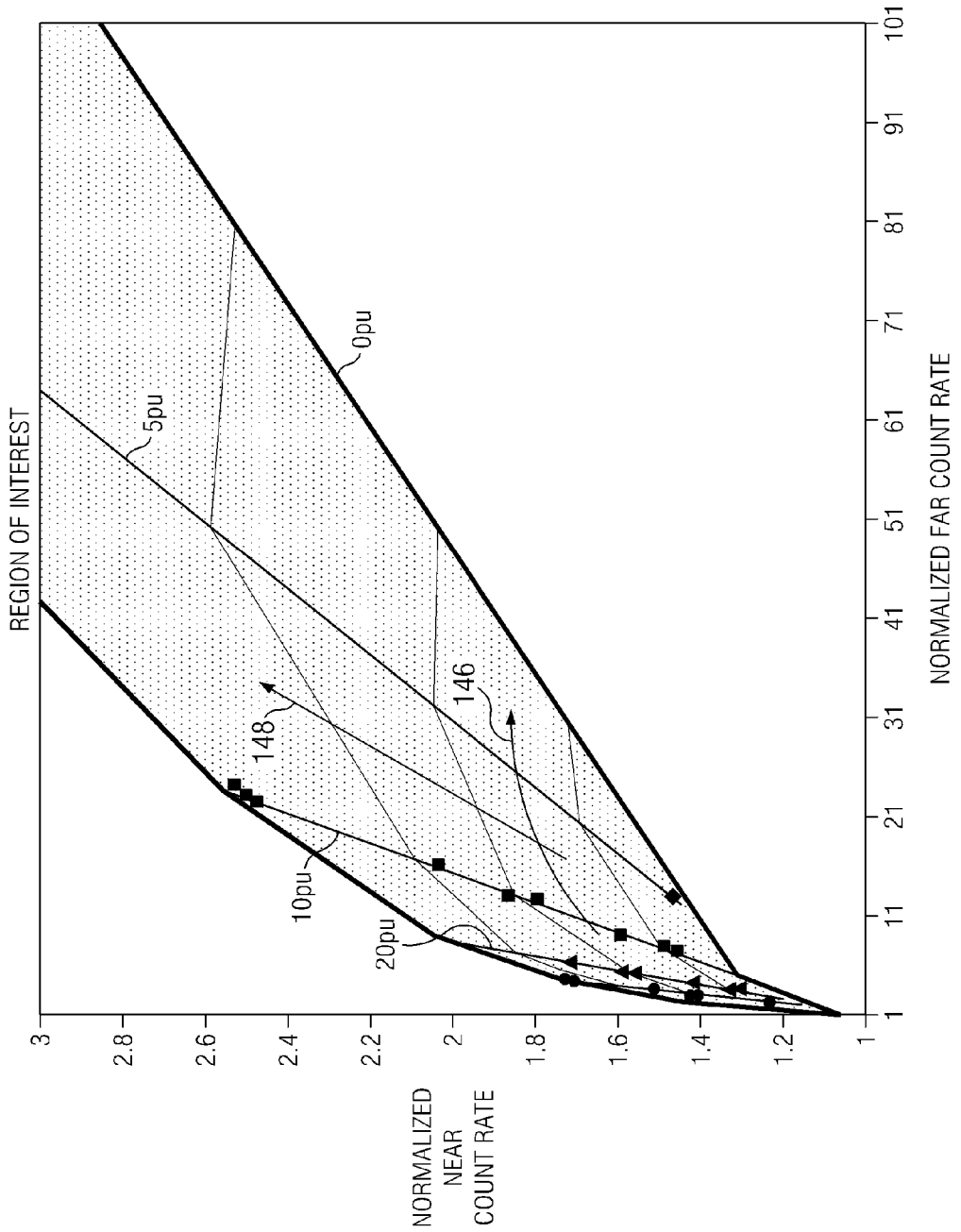
FIG. 4 depicts a contour plot of formation porosity for the simulated data depicted on FIGS. 3A and 3B.

The region of interest depicted on FIGS. 3A and 3B is generally realistic in subterranean logging operations and is commonly on the order of a two or three inch borehole enlargement for a typical logging while drilling application. For example, the region of interest in a six inch specified borehole may include a borehole diameter in the range from about six to about nine inches and a sensor standoff in the range from about zero to about two inches. FIG. 4 depicts one exemplary region of interest in average near counts versus average far counts for the simulations depicted on FIGS. 3A and 3B. FIG. 4 may be further thought of as a contour map including porosity and borehole geometry contours as a function of the near count rate and the far count rate. The directions of decreasing porosity and decreasing borehole geometry parameter are indicated at 146 and 148.

While not shown on FIGS. 3A and 3B, several other environmental effects were also simulated. In particular, the effect of mud weight (or density), salinity, and pressure was also investigated. At mud weights of 14 and 18 pounds per gallon (as compared to 8.3 pounds per gallon for water), at a mud salinity of 200,000 parts per million, and at a borehole fluid density changes due to a pressure of 25,000 psi and a temperature of 250 degrees F., the near and far count rates fell near or on the aforementioned lines at each of the indicated formation porosities. The invention may therefore be advantageously implemented with little or no mud weight, salinity, and pressure corrections.

Figure 5:
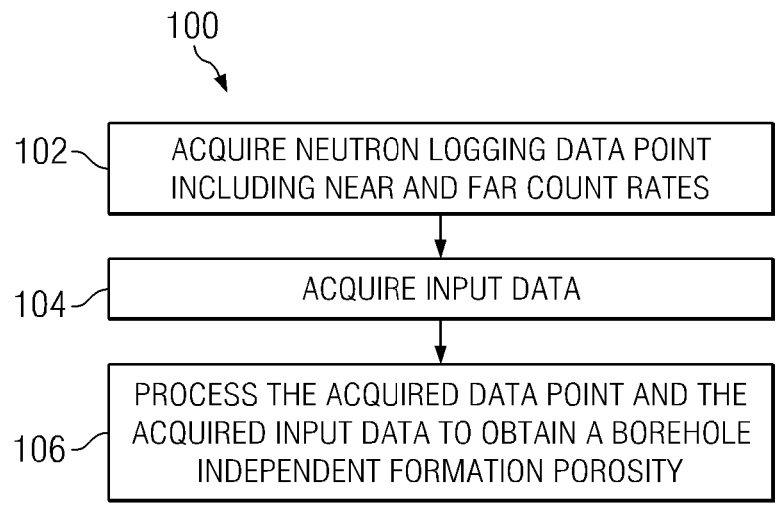
FIG. 5 depicts a flow chart of one exemplary method embodiment in accordance with the present invention.

FIG. 5 depicts a flow chart of one exemplary method embodiment 100 in accordance with the present invention. At 102 a neutron logging data point is acquired including, for example, an average near count rate and an average far count rate. At 104, input data is acquired. The input data relates near count rate, far count rate, and formation porosity in the region of interest (i.e., within predetermined ranges of borehole diameter and sensor standoff). At 106, the data point acquired at 102 is processed in combination with the curves acquired 104 to obtain a borehole independent formation porosity.

The neutron logging data point acquired at 102 preferably includes 'average' count rates (an average near detector count rate and an average far detector count rate). The use of such average count rates tends to average the effects of variable sensor standoff during rotation of the logging tool and therefore tends to decrease the sensitivity of the method to the position of the logging tool in the borehole. By average it is meant that the data is preferably acquired over a time interval greater than or equal to the rotational period of the logging tool in the borehole. For example, in one exemplary embodiment, near and far detector neutron counts may be acquired over a single, relatively long time interval (e.g., ten seconds). The count rates may then be computed by dividing the number of detected neutrons (the counts) by the length of the time interval. In another embodiment, near and far detector neutron counts may be acquired over a number of relatively short time intervals. For example, in one LWD embodiment, near and far detector count rates may be acquired at 10 millisecond intervals. A plurality of these count rates may then be averaged over a longer time period (e.g., 1000 count rates obtained over a time period of 10 seconds) to obtain average count rates during rotation of the tool in the borehole. The invention is not limited to any particular means of acquiring average neutron count rates. Nor is the invention even limited to the use of average count rates.

As described above, the input data acquired at 104 relates near count rate, far count rate, and formation porosity in the region of interest (i.e., within predetermined ranges of borehole diameter and sensor standoff). The input data may include, for example, a plurality of curves (e.g., lines) corresponding to a plurality of formation porosity values (e.g., as depicted on FIGS. 3A and 3B). Each curve indicates changes in the near count rate and far count rate with changes in borehole diameter and sensor standoff at a particular formation porosity. These curves may be acquired in substantially any suitable form, for example, in the form of plots as indicated on FIGS. 3A and 3B or in the form of a contour map as indicated on FIG. 4. The input data may also be represented mathematically, for example as a plurality of mathematical coefficients. The invention is not limited in regards to the form in which the input data are obtained. As described in more detail below with respect to FIGS. 7, 8, and 9, the input data may also include a plurality of porosity intercept points and a relationship between a slope and the borehole independent formation porosity.

In one exemplary embodiment suitable for electronic processing (e.g., on a surface computer or a downhole controller), the input data may be represented by a plurality of mathematical coefficients. For example only, the near count rate may be expressed as a linear function of the far count rate (as depicted on FIGS. 3A and 3B—although the invention is not limited in this regard). Such linearity may be represented mathematically, for example, as follows:

$$C_N = \alpha_s \cdot C_F + \beta_I \qquad \text{Equation 1}$$

where $C_N$ and $C_F$ represent the near and far count rates, $\alpha_s$ represents the slope of the line, and $\beta_I$ represents the intercept on the near count rate axis. It will be understood based on the foregoing discussion with respect to FIGS. 3 and 4 that the coefficients $\alpha_s$ and $\beta_I$ are functions of the borehole independent formation porosity. In one exemplary embodiment of the invention, these functions may be approximated as polynomials, for example, as follows:

$$\alpha_s = f_s(\text{por}) \approx a_s \text{por}^3 + b_s \text{por}^2 + c_s \text{por} + d_s \qquad \text{Equation 2}$$

$$\beta_I = f_I(\text{por}) \approx a_I \text{por}^3 + b_I \text{por}^2 + c_I \text{por} + d_I \qquad \text{Equation 3}$$

where por represents the borehole independent formation porosity, $a_s$, $b_s$, $c_s$, and $d_s$ represent the polynomial coefficients for the slope and $a_I$, $b_I$, $c_I$, and $d_I$ represent the polynomial coefficients for the intercept. Those of ordinary skill in the art will readily appreciate that the polynomial coefficients may be acquired at 104 from simulated data, empirical data, or a combination of simulated and empirical data. Substitution of Equations 2 and 3 into Equation 1 results in an equation relating the near and far count rates by a single unknown (the borehole independent formation porosity).

$$C_N (a_s \text{por}^3 + b_s \text{por}^2 + c_s \text{por} + d_s) \cdot C_F + a_I \text{por}^3 + b_I \text{por}^2 + c_I \text{por} + d_I \qquad \text{Equation 4}$$

After substituting the data point acquired at 102 (i.e., the near and far count rates) into Equation 4, the porosity por may be solved for directly. It will be understood that Equation 4 (or another similarly derived equation) may be readily solved using conventional root finding algorithms. Such algorithms are available, for example, via commercial software such as Mathematica® (Wolfram Research, Inc., Champaign, Ill.). Equation 4 may also be solved using look up tables and/or graphical methods (e.g., a contour plot as depicted on FIG. 4).

It will of course be understood that the invention is not limited to the use of a polynomial equation or polynomial coefficients. The relationship between the near and far count rates and the borehole independent formation porosity may be approximated using mathematical equations having substantially any suitable form. The invention is not limited in these regards.

In alternative embodiments, the present invention makes use of the realization that the slope of the lines indicated on FIGS. 3A and 3B is both a strong function of the formation porosity and substantially independent of borehole conditions including borehole diameter (or caliper) and sensor standoff. These slopes may therefore be thought of as being borehole independent slopes (i.e., the slopes are independent of the borehole diameter and sensor standoff within the aforementioned region of interest). As a result, it was further realized that a determination of a borehole independent slope may enable a subsequent determination of a formation porosity that is substantially independent of the aforementioned borehole conditions (a substantially borehole independent formation porosity).

Figure 6:
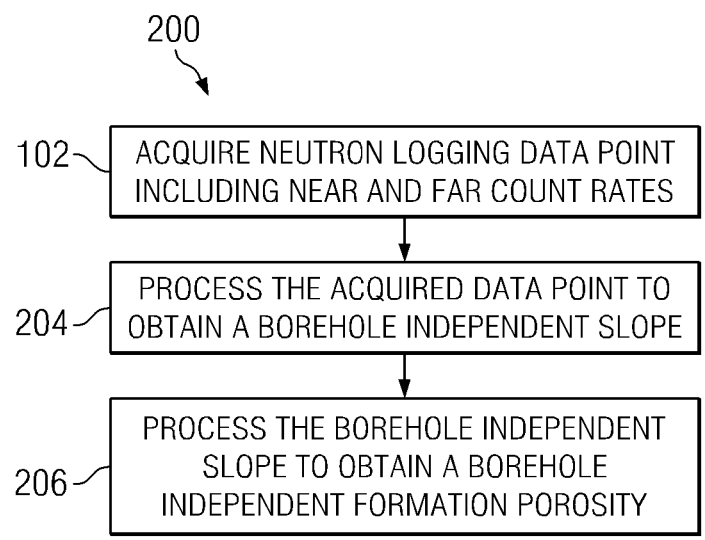
FIGS. 6 and 7 depict flow charts of alternative method embodiments in accordance with the present invention.
Figure 7:
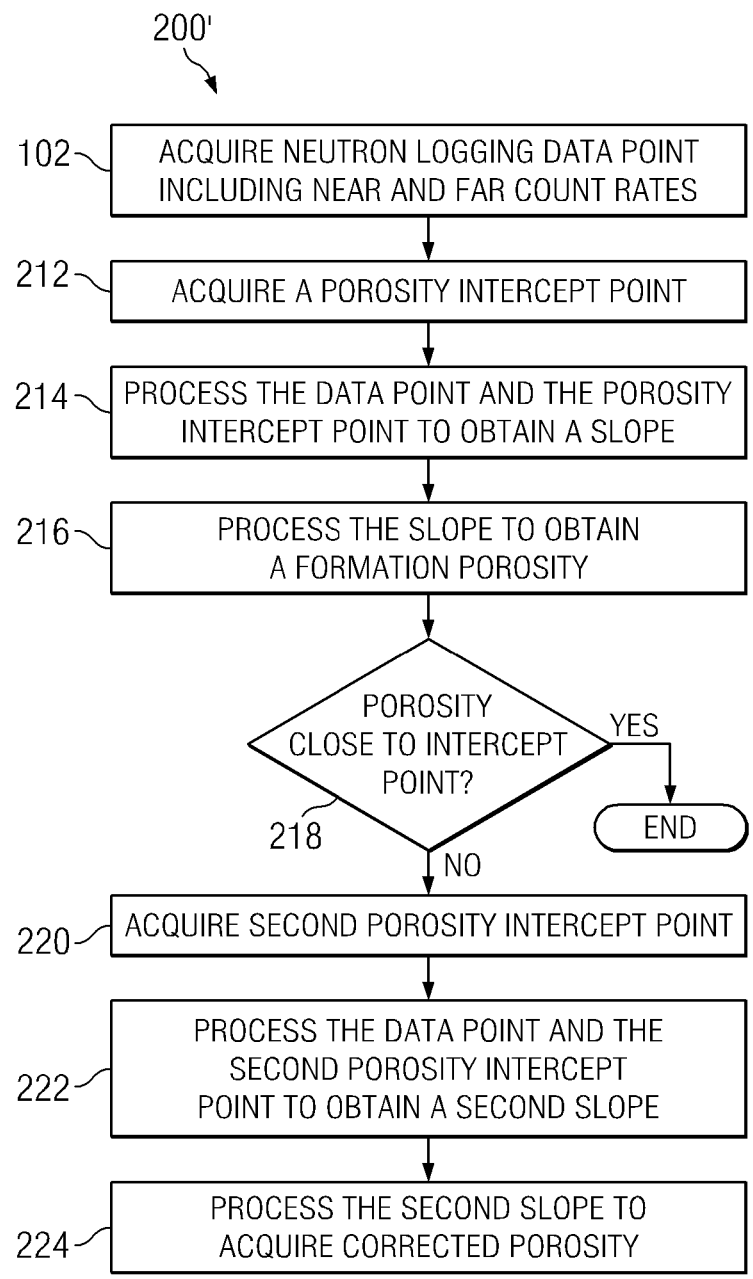
Figure 8:
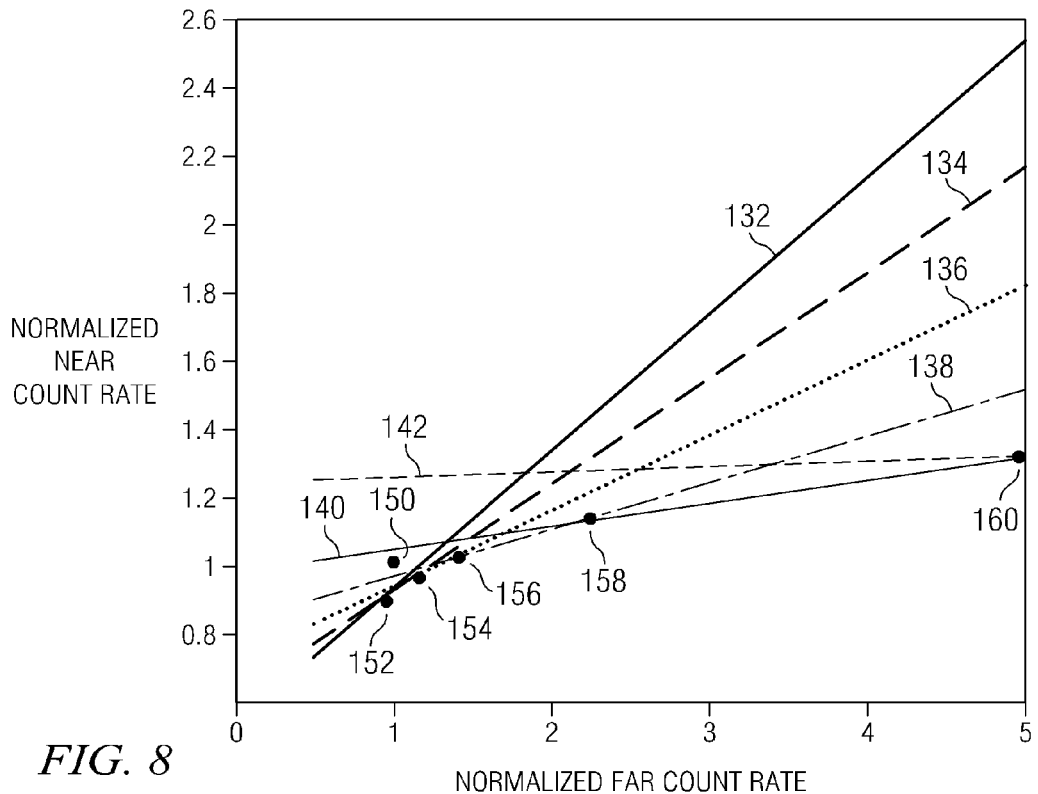
FIG. 8 depicts a plot of average near count rate versus average far count rate indicating intercept points of the simulated data shown on FIGS. 3A and 3B.

FIGS. 6 and 7 depict flow charts of alternative method embodiments 200 and 200' in accordance with the present invention. At 102 a neutron logging data point is acquired including, for example, an average near count rate and an average far count rate (as described above with respect to FIG. 5). In method 200 (FIG. 6), the data point is processed at 204 to obtain a borehole independent slope which is in turn further processed 206 to obtain a borehole independent formation porosity. The borehole independent slope may be obtained at 204, for example, by acquiring a second point along the line. In method 200' (FIG. 7), this second point is referred to as a porosity intercept point (as described in more detail below with respect to FIG. 8). The porosity intercept point is acquired at 212 and processed at 214 in combination with the data point acquired at 102 to obtain a slope. The slope is further processed at 216 to obtain a formation porosity. If the porosity computed at 216 is sufficiently close (as checked at 218) to a porosity range for which the porosity intercept point was obtained then the slope may be thought of as being the borehole independent slope and the porosity computed at 216 may be taken to be the borehole independent formation porosity. Otherwise, a second porosity intercept point may be acquired at 220. The second porosity intercept point may be processed at 222 in combination with the neutron logging data point acquired at 102 to obtain a second slope, which may be in turn further processed at 224 to acquire a corrected formation porosity (the borehole independent formation porosity).

Those of ordinary skill in the art will readily appreciate that the neutron logging data point acquired at 102 represents a single point in a plot of near versus far count rates (including a single near count rate and a single far rate). In the exemplary method embodiment described above with respect to FIG. 7, the borehole independent slope is obtained using an additional point, taken, for example, to be the intercept of any two of the lines 132, 134, 136, 138, 140, and 142 in FIGS. 3A and 3B. As depicted on FIG. 8, these lines do not generally intercept at a single point. Nor do they intercept at the water point 150. In particular, the intercept of lines 132 and 134 (indicative of 50 and 40 pu) is shown at 152. The intercept of lines 134 and 136 (indicative of 40 and 30 pu) is shown at 154. The intercept of lines 136 and 138 (indicative of 30 and 20 pu) is shown at 156. The intercept of lines 138 and 140 (indicative of 20 and 10 pu) is shown at 158. And the intercept of lines 140 and 142 (indicative of 10 and 0 pu) is shown at 160.

In preferred embodiments of the invention, a high porosity intercept point is selected at 212 (FIG. 7). For example, intercept point 152 (representative of an intercept between 40 and 50 pu) may be advantageously selected. The acquired data point and intercept point 152 may be utilized to calculate a borehole independent slope, for example, as follows:

$$\text{slope} = \frac{D_N - I_N}{D_F - I_F} \qquad \text{Equation 5}$$

where $D_N$ and $D_F$ represent the near and far count rates of the acquired data point and $I_N$ and $I_F$, represents the near and far count rates at the selected intercept point (e.g., intercept point 152). It will be understood that the near and far count rates at the selected intercept point may be determined from simulated data, empirical data, or a combination of simulated and empirical data. The invention is not limited in these regards.

Figure 9:
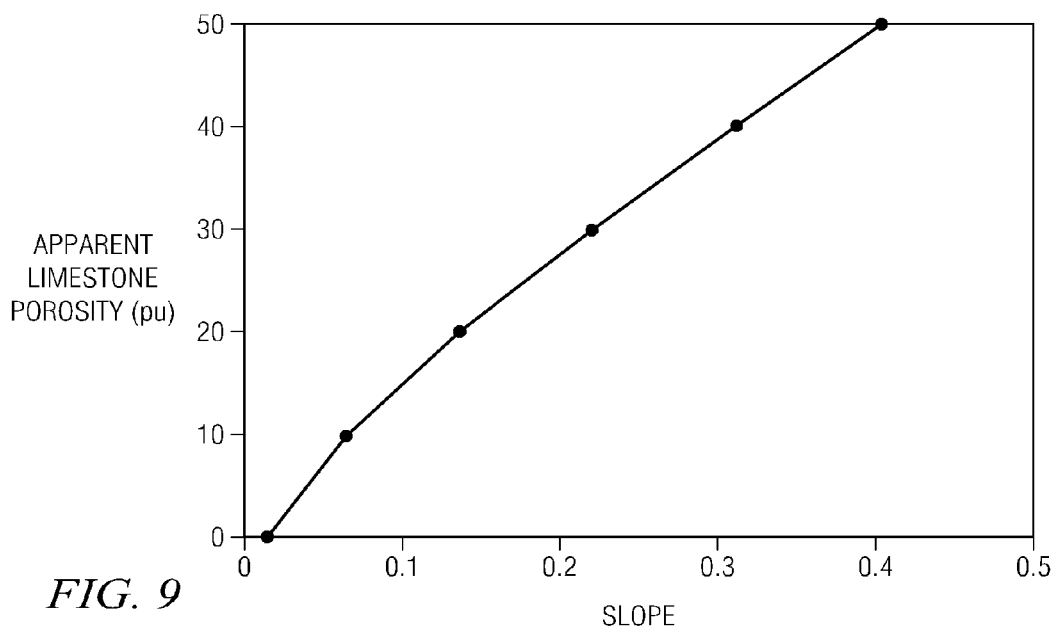
FIG. 9 depicts a plot of borehole independent limestone porosity versus slope for the simulated data shown on FIGS. 3A and 3B.

The formation porosity may be computed from the slope, for example, as follows:

$$porosity = f(slope) \quad \text{Equation 6}$$

where $f(slope)$ indicates that the porosity is a mathematical function of the previously computed slope. The function $f$ may be approximated, for example, using a polynomial function or substantially any other suitable mathematical function. FIG. 9 depicts a plot of borehole independent limestone porosity (in pu) versus borehole independent slope acquired from the simulated data depicted on FIGS. 3A and 3B. As indicated, the borehole independent limestone porosity increases essentially monotonically with increasing slope.

It will be understood that the invention is not limited to a mathematical expression (or even the use of a mathematical formula). The formation porosity may be estimated from the obtained slope using substantially any suitable means, for example, including a look-up table, a transformation, graphical methods, an empirical mathematical expression, and the like. Again, the invention is not limited in these regards.

In one exemplary embodiment of the invention, a piece-wise algorithm may be implemented. For example, a first intercept point may be utilized for a porosity that is expected to be in a first range (e.g., from about 20 to about 50 pu) and a second intercept point may be utilized for a porosity that is expected to be in a second range (e.g., from about 0 to about 20 pu). Moreover, the piece-wise algorithm may include substantially any suitable number of expected porosity ranges (e.g., first, second, and third or even first, second, third, and fourth ranges).

In an alternative embodiment, the formation porosity may be determined in an iterative fashion. A first intercept point may be used to determine a first slope and a first porosity (e.g., at 110 and 112 in method 100'). The first porosity may then be compared at 114 with a porosity range from which the first intercept point was obtained. If the first porosity is in a suitable range then it may be taken to be the borehole independent formation porosity. When the first porosity is outside the suitable range, a second intercept point may be selected and used to determine a second slope and a corrected porosity (e.g., at 116, 118, and 120 of method 100'). The second slope and second porosity are typically taken to be the borehole independent slope and the borehole independent porosity.

This iterative embodiment is now described further with respect to the following non-limiting example. Intercept point 152 (indicative of an intercept between 40 and 50 pu) may be used in combination with the acquired data point to compute the first slope and the first formation porosity. If the first formation porosity is greater than or equal to 30 pu, then the first porosity can be taken to be the borehole independent formation porosity (with no further iterations being required). If the first porosity is less than 30 pu, then a second intercept point may be selected based upon the value of the first porosity. For example, when the first porosity is in the range from 15 to 30 pu, intercept point 158 (indicative of an intercept between 10 and 20 pu) may be used as the second intercept point. When the first porosity is in the range from 0 to 15 pu, intercept point 160 (indicative of an intercept between 0 and 10 pu) may be used as the second intercept point. The second intercept point and the acquired data point are then used to compute a second slope and a corrected porosity as described above with respect to FIG. 5. A single iteration is typically suitable to determine a highly accurate borehole independent formation porosity, however, the invention is not limited in this regard. Substantially any number of iterations may be implemented.

Figure 10A:
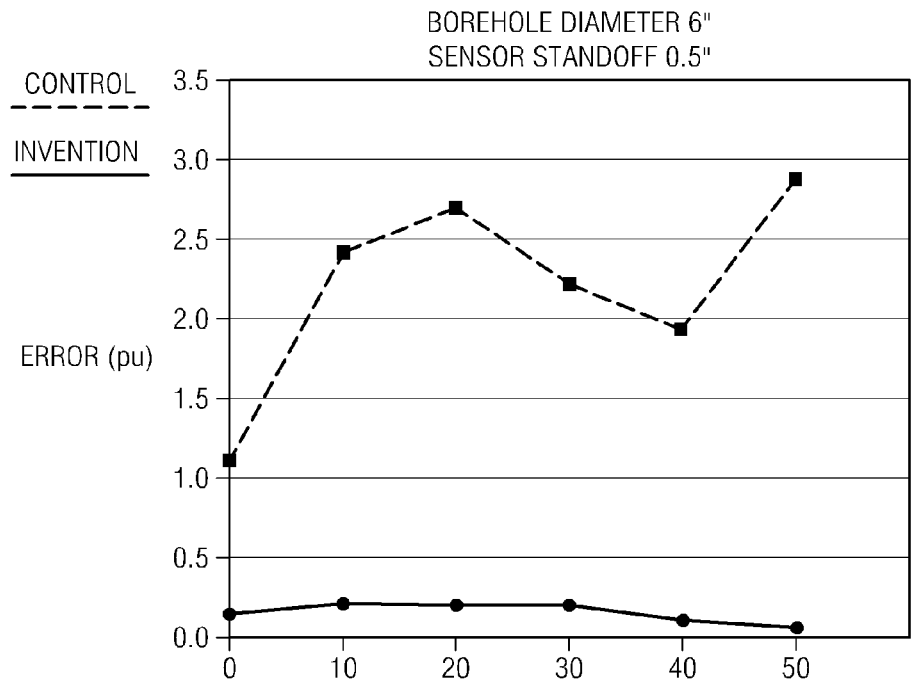
FIGS. 10A through 10D (collectively FIG. 10) depict plots of error effects versus formation porosity for multiple non standard borehole diameter and sensor standoff values.
Figure 10B:
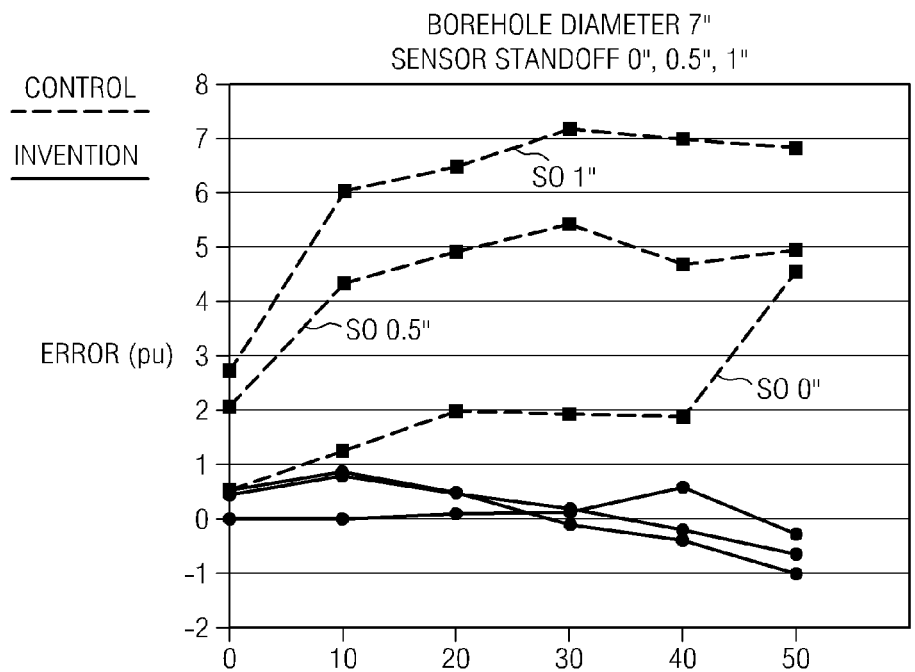
Figure 10C:
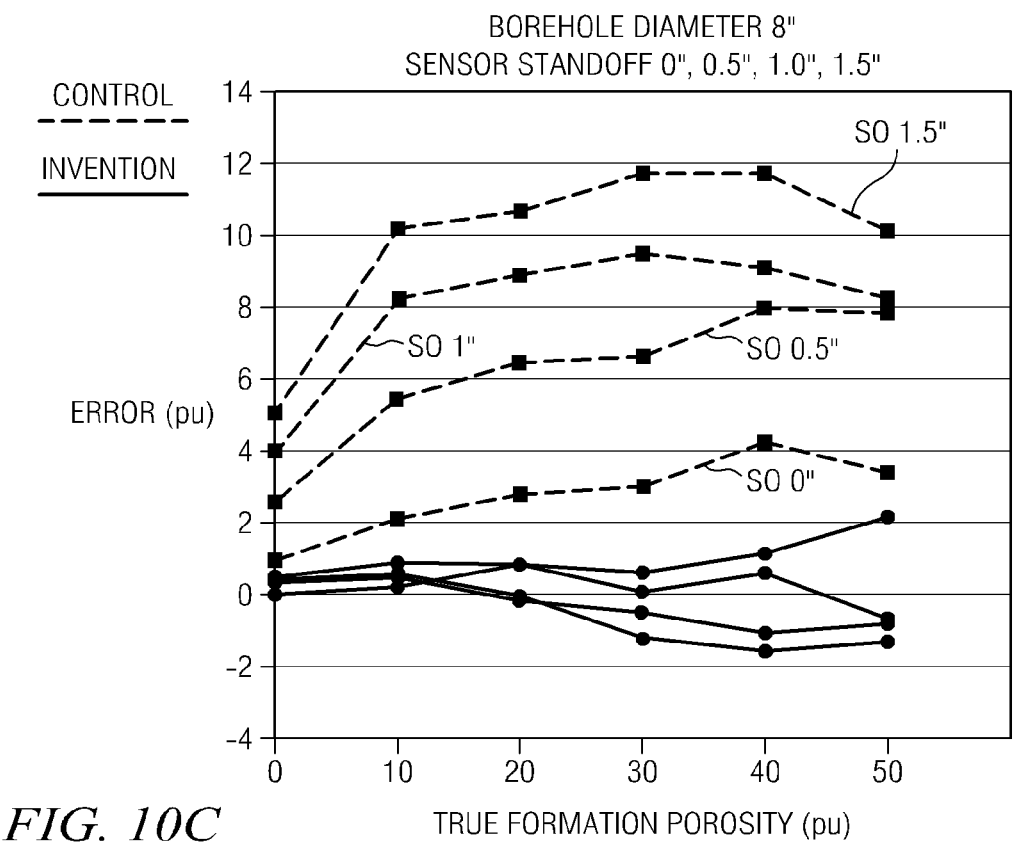
Figure 10D:
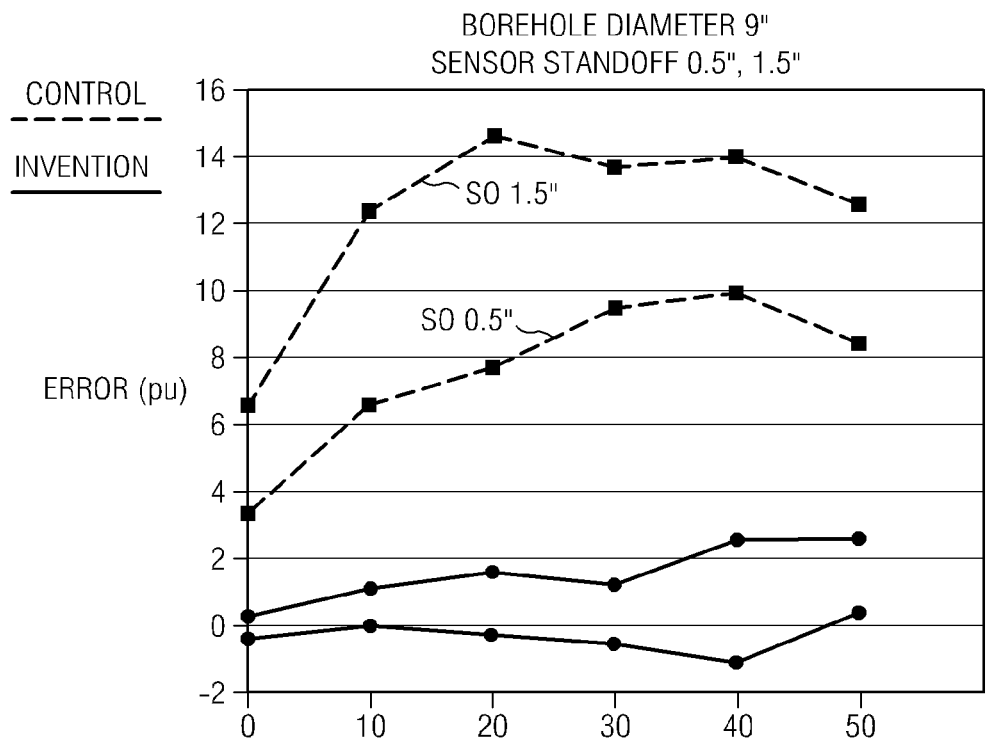

FIGS. 10A through 10D depict plots of error effects versus formation porosity for multiple non-standard borehole diameter and sensor standoff values. These FIGURES contrast one example of the inventive method with conventional ratio processing (the control). FIG. 10A plots the error effects for a borehole diameter of 6 inches and a sensor standoff of 0.5 inches. FIG. 10B plots the error effects for a borehole diameter of 7 inches and sensor standoffs of 0, 0.5, and 1 inch. FIG. 10C plots the error effects for a borehole diameter of 8 inches and sensor standoffs of 0, 0.5, 1, and 1.5 inches. FIG. 10D plots the error effects for a borehole diameter of 9 inches and sensor standoffs of 0.5 and 1.5 inches.

With further reference to FIGS. 10A-10D, the inventive method shows significantly reduced error as compared to the convention ratio processing methodology. At borehole diameters of 6 and 7 inches (FIGS. 10A and 10B) the maximum error is less than 1 pu as compared to greater than 7 pu for the conventional ratio methodology. At borehole diameters of 8 and 9 inches (FIGS. 10C and 10D) the maximum error is about 2 pu as compared to greater than 14 pu for the conventional ratio methodology.

It should be emphasized that the improvements depicted on FIGS. 10A-10D may be advantageously achieved without any knowledge of borehole size or sensor standoff (i.e., without the need to make any standoff and/or caliper measurements during the logging operation). On the contrary, conventional correction algorithms require such measurements and are therefore limited by their accuracy and reliability. The present invention advantageously has no such limitations and therefore tends to significantly improve the reliability neutron porosity measurements.

It will be understood that while the exemplary embodiments are described above with respect to a simulated limestone formation, the invention is not limited in these regards. Exemplary embodiments of the invention are applicable to substantially any formation lithology encountered in conventional subterranean logging operations. As is well known to those of ordinary skill in the art, limestone, sandstone, and dolomite are the three primary lithologies that are commonly distinguished in conventional neutron logging operations. Conventional neutron logs are typically presented on either a limestone or a sandstone scale, meaning that they are intended to indicate the correct porosity values in either water-bearing limestone or sandstone. Conversion charts and algorithms are readily available for converting from one lithology scale to another (e.g., from sandstone or limestone to another lithology such as clay). Neutron logs can be acquired in substantially any subterranean formation and the response of the log to other (e.g., various clays) minerals may be useful for the purpose of evaluating the formation.

Figure 11A:
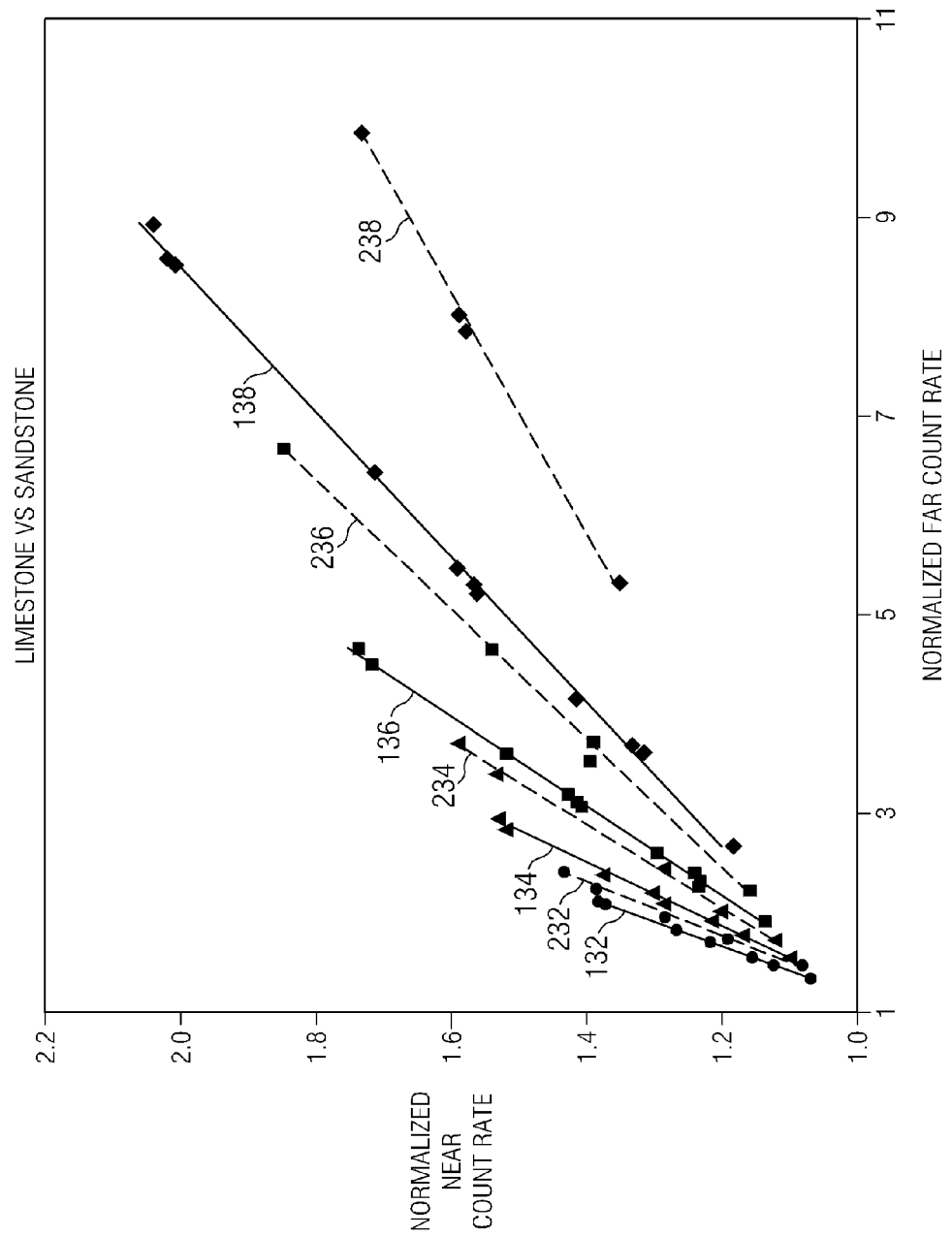
FIG. 11A depicts simulated data in a plot of average near count rate versus average far count rate for limestone and sandstone formations.

FIG. 11A depicts a plot of average near count rate versus average far count rate for limestone and sandstone formations. The limestone formations are depicted at 132, 134, 136, and 138 as described above with respect to FIG. 3A. The sandstone formations are depicted at 232, 234, 236, and 238 for porosity values of 50, 40, 30, and 20 pu. The sandstone formations are similar to the previously discussed limestone formations in that each formation porosity results in a substantially linear plot when the borehole diameter and sensor standoff vary within a certain range. At any given porosity (e.g., in the range from 20 to 50 pu), the slope of the borehole independent line corresponding to the sandstone formation is less than that of the limestone formation.

Figure 11B:
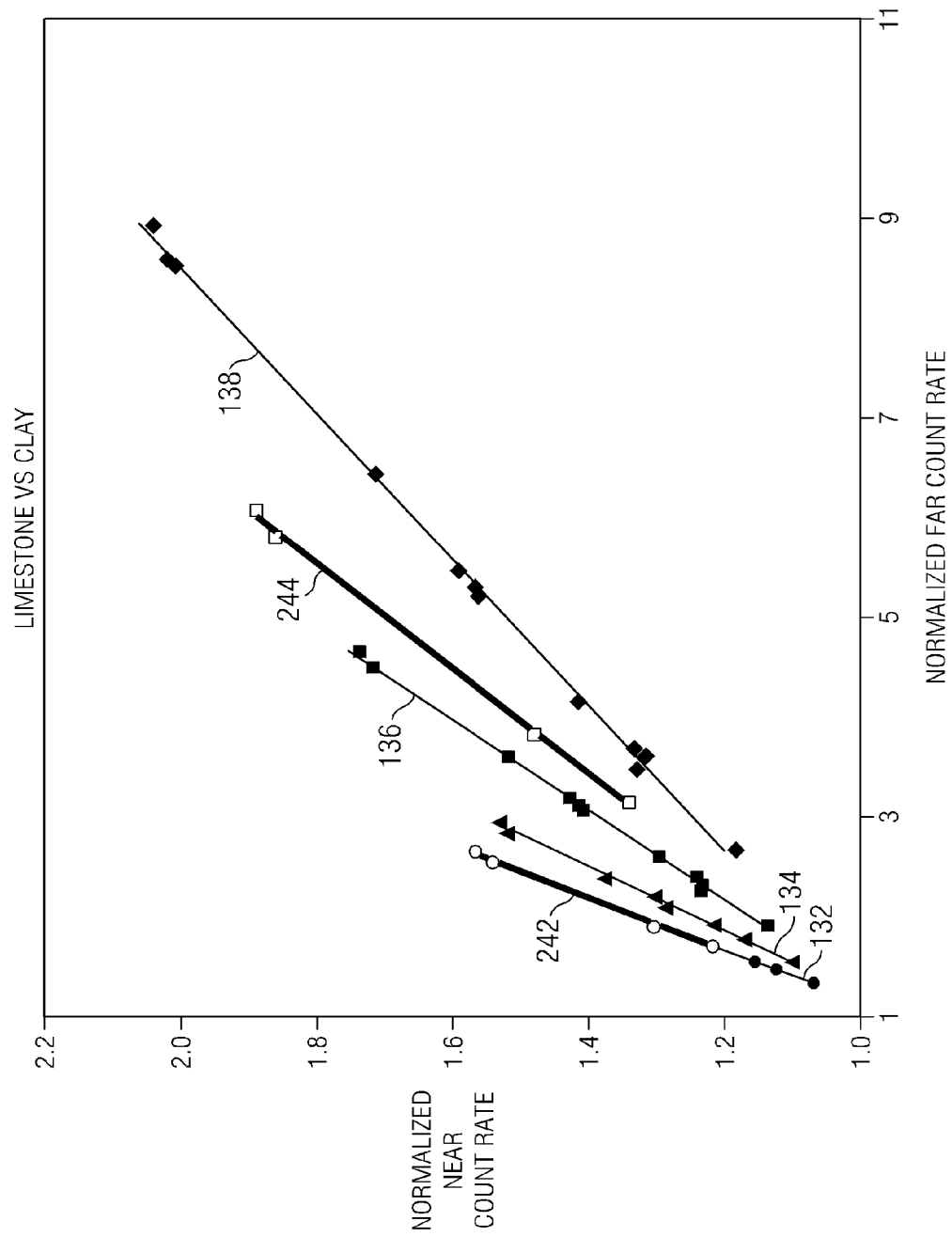
FIG. 11B depicts simulated data in a plot of average near count rate versus average far count rate for limestone and clay (illite and kaolinite) formations.

FIG. 11B depicts a plot of average near count rate versus average far count rate for limestone and clay (illite and kaolinite depicted at 242 and 244) formations. The clay formations 242 and 244 are similar to the previously discussed limestone formations in that the plot is substantially linear when the borehole diameter and sensor standoff vary within a certain range.

It will be understood that method embodiments in accordance with the present invention may be implemented either uphole (e.g., by an operator at the surface or on a surface computer) or downhole (e.g., by a downhole controller). The invention is in no way limited in these regards. Moreover, it will be further understood that the aspects and features of the present invention may be embodied as logic that may be processed by, for example, a computer, a microprocessor, hardware, firmware, programmable circuitry, or any other processing device well known in the art. Similarly the logic may be embodied on software suitable to be executed by a processor, as is also well known in the art. The invention is not limited in this regard. The software, firmware, and/or processing device may be included, for example, on a downhole assembly in the form of a circuit board, on board a sensor sub, or MWD/LWD sub. Alternatively the processing system may be at the surface and configured to process data sent to the surface by sensor sets via telemetry or data link systems known in the art. Electronic information such as logic, software, or measured or processed data may be stored in memory (volatile or non-volatile), or on conventional electronic data storage devices such as are well known in the art.

Although the present invention and its advantages have been described in detail, it should be understood that various changes, substitutions and alternations can be made herein without departing from the spirit and scope of the invention as defined by the appended claims.

We claim:

1. A method for estimating formation porosity from a neutron logging measurement, the method comprising:
   (a) acquiring a neutron logging data point including a near detector count rate in a formation and a far detector count rate in the formation, wherein the neutron logging data point comprises average near detector count rates and average far detector count rates, the average near count rates and the average far detector count rates obtained by averaging near and far detector counts over a time period greater than or equal to a rotational period of a logging tool in a borehole;
   (b) acquiring input data, the input data relating near count rate, far count rate, and formation porosity in a region of interest, wherein the region of interest comprises a predetermined range of borehole diameter and a predetermined range of sensor standoff; and
   (c) causing a processor to process the data point acquired in (a) and the input data acquired in (b) to obtain a borehole independent formation porosity measurement, wherein the porosity measurement is substantially independent of borehole diameter, borehole shape and sensor standoff; and
   (d) continuing hydrocarbon exploration and/or hydrocarbon production based on the porosity measurement.

2. The method of claim 1, wherein the input data acquired in (b) comprises a plurality of curves, the curves indicating the dependence of the near detector count rate and the far detector count rate on the borehole diameter and the sensor standoff in the region of interest, each curve corresponding to a unique formation porosity.

3. The method of claim 2, wherein the curves are lines.

4. The method of claim 1, wherein the input data comprises a plurality of coefficients, the coefficients indicating the dependence of the near count rate and the far count rate on the borehole diameter and sensor standoff in the region of interest as a function of formation porosity.

5. The method of claim 1, wherein the input data comprises a contour map, the contour map indicating the dependence of the near count rate and the far count rate on the borehole diameter and sensor standoff in the region of interest as a function of formation porosity.

6. A neutron logging tool comprising:
   a logging tool body;
   a neutron source deployed in the tool body;
   first and second, near and far neutron detectors deployed in the tool body and longitudinally spaced apart from one another and from the neutron source;
   a controller configured to (i) acquire a neutron logging data point including first near and far detector count rates in a formation from the near and far neutron detectors, (ii) acquire input data, the input data relating near count rate, far count rate, and formation porosity in a region of interest, the region of interest including a predetermined range of borehole diameter and a predetermined range of sensor standoff, and (iii) processing the acquired data point and the acquired input data to obtain a borehole independent porosity, wherein the controller is configured to obtain the first near and far detector count rates by averaging near and far detector counts over a time period greater than or equal to a rotational period of the tool in a borehole, and substantially independent of borehole diameter, borehole shape and sensor standoff.

7. The neutron logging tool of claim 6 being a logging while drilling tool.

8. The neutron logging tool of claim 6, wherein the input data comprises a plurality of coefficients, the coefficients indicating the dependence of the near count rate and the far count rate on the borehole diameter and sensor standoff in the region of interest as a function of formation porosity.

* * * * *